United States Patent [19]

Nelson

[11] 4,031,143

[45] June 21, 1977

[54] REDUCTION USING NaAlEt$_2$H$_2$

[75] Inventor: Gunner E. Nelson, Baton Rouge, La.

[73] Assignee: Ethyl Corporation, Richmond, Va.

[22] Filed: Mar. 5, 1973

[21] Appl. No.: 337,902

[52] U.S. Cl. .......................................... 260/632 D
[51] Int. Cl.$^2$ ......................................... C07C 29/00
[58] Field of Search ........ 260/638 A, 638 R, 632 D

[56] References Cited

UNITED STATES PATENTS

| | | | |
|---|---|---|---|
| 3,153,076 | 10/1964 | Wood et al. | 260/632 D |
| 3,184,492 | 5/1965 | Cole | 260/638 R |
| 3,281,443 | 10/1966 | Hunt | 260/638 A |
| 3,412,127 | 11/1968 | Napier | 260/632 D |
| 3,686,248 | 8/1972 | Nelson | 260/448 A |

*Primary Examiner*—Joseph E. Evans

*Attorney, Agent, or Firm*—Donald L. Johnson; John F. Sieberth; Shelton B. McAnelly

[57] ABSTRACT

It is disclosed that a process wherein a reducible compound is reduced by an addition reaction to aluminum dihydrocarbon dihydrides of sodium, potassium or lithium followed by hydrolysis to remove the aluminum is improved by subjecting to oxidation with molecular oxygen the product from the aluminum addition prior to the hydrolysis operation. The intervening oxidation operation converts al—R bonds in the addition product into al—O—R bonds, R being hydrocarbon, preferably alkyl, the result being that upon hydrolysis an alcohol is produced from those groups rather than a hydrocarbon. The by-product alcohol thus produced is easier to dispose of without serious ecological disadvantages which is a significant improvement over the situation that exists when hydrocarbon is released.

4 Claims, No Drawings

REDUCING USING NaAlEt$_2$H$_2$

BACKGROUND OF THE INVENTION

1. Field of the Invention

This invention relates to the reduction of reducible compounds with aluminum dihydrocarbon dihydrides of sodium, potassium or lithium as reducing agents.

2. Description of the Prior Art

The production of sodium aluminum diethyl dihydride and its use as a reducing agent is described in U.S. Pat. No. 3,686,248. It is disclosed in that patent that sodium aluminum diethyl dihydride is an excellent, mild and selective reducing agent for various compounds such as those containing carbonyl, nitrile or amide groups.

Although the fundamental addition reaction takes place smoothly as does the succeedant hydrolysis reaction, one difficulty experienced in the use of sodium aluminum diethyl dihydride and like reducing agents is that the complexes formed by the addition to the al—H bonds of the aluminum compound of the functional groups being reduced also contain al—R bonds which on hydrolysis, as for example with water in neutral, basic or acidic environment, yield hydrocarbon. Although such hydrocarbon liberation might at one time have been considered inconsequential, the advent of environmental concern and controls and limitation upon the release of hydrocarbons to the atmosphere raises certain problems. In short, it would be desired to avoid or minimize the liberation of hydrocarbon connected with the use of sodium aluminum diethyl dihydride and like reducing agents.

Accordingly, it is an object of the present invention to provide a process whereby the production of volatile hydrocarbons in the course of reductions using aluminum dihydrocarbon dihydrides of sodium, potassium or lithium is materially reduced or avoided altogether.

SUMMARY

In accordance with the present invention, it has been discovered that the liberation of hydrocarbons in the course of reduction reactions using sodium aluminum diethyl dihydride and related compounds can be substantially reduced or eliminated entirely by performing an oxidation of the al—R, (al—C$_2$H$_5$) for example, containing product from the addition step prior to the final step of hydrolysis of the aluminum addition compounds. The oxidation is performed easily at moderate temperatures utilizing molecular oxygen. The precise form of molecular oxygen is not critical. It may be supplied as air, or air diluted with an inert gas such as nitrogen or carbon dioxide, or the like. In the course of the oxidation, oxygen is inserted between the al and the C$_2$H$_5$ of the al—C$_2$H$_5$ groups to produce aluminum alkoxide groups (al—O—C$_2$H$_5$). The formation of such al—O—C$_2$H$_5$ and related groups provides the desirable result that in the hydrolysis operation, the C$_2$H$_5$—O portion combines with hydrogen from water used in the hydrolysis to form an alcohol (ethyl) which is water-soluble and which has a much higher boiling point than ethane and which is liquid at ordinary temperature. The result is that the liberation of volatile or gaseous hydrocarbons is eliminated or substantially reduced alleviating ecological problems attendant to the liberation of ethane and like hydrocarbons.

Accordingly, the invention is directed to an improvement in a process for reducing a reducible compound by an addition reaction to NaAlEt$_2$H$_2$ followed by hydrolysis to remove the aluminum and recovering a reduced product. In the improvement of the present invention, the product from the addition reaction is subjected to oxidation with molecular oxygen prior to the hydrolysis whereby al—C$_2$H$_5$ bonds contained therein are converted to al—O—C$_2$H$_5$ bonds.

In a preferred aspect, the oxidation is performed at a temperature of from about −25° C to about 200° C; preferably at a temperature of from 0° C to about 100° C; especially at a temperature of from about 25° C to about 50° C.

The oxidation of aluminum alkyls is an operation well known and purposely used in the aluminum chemistry technology for the production of alcohols. The process can be conducted over a wide range of temperature, pressure and other conditions using a wide variety of oxidation reactants, in one or more steps at similar or different conditions in each step, continuously or batchwise, with or without catalysts and the like. Typical patents disclosing the operation and various considerations connected therewith are U.S. Pat. Nos. 2,892,858; 3,384,651; 3,394,195; 3,415,861; 3,475,476; 3,487,097; 3,557,236; 3,575,501; and 3,655,520.

The oxidation proceeds readily at ordinary temperatures and pressures such as about room temperature and about atmospheric pressure; however, as is evident from the prior art, numerous procedures are known for improving the oxidation in various situations and for minimizing side reactions of an undesired nature. It is obvious that the oxidation is desirably conducted under conditions which do not adversely affect the compounds present and preferably avoid the existence of explosive mixtures. The oxidation is also suitably conducted at temperatures and pressures above or below ordinary.

Thus, in general, the oxidation may be conducted at temperatures down to the freezing point of sodium aluminum diethyl dihydride or solutions thereof. As an example, the freezing point of a 26 percent solution of NaAl(C$_2$H$_5$)$_2$H$_2$ in toluene is approximately −35° C. On the other hand, the oxidation may be conducted at temperatures up to the decomposition temperature which generally is in excess of 200° C such as 250° C, or even higher. A narrower temperature range of operation is from about −25° C to about 200° C with a temperature of from about 0° to about 100° C being preferred, particularly from about 25° to about 50° C.

Pressures preferably are from about atmospheric up to about 5 atmospheres based on extrinsic considerations to avoid the use of expensive high pressure or high vacuum equipment; however, in instances where pressure operation is desired as for control of vaporization and the like or because of co-present materials as shown in the prior art cited herein, super-atmospheric or sub-atmospheric pressures may be used.

Typical oxidant mixtures include air, air diluted with various amounts of nitrogen or other inert diluent such as carbon dioxide or recycled off-gas from the oxidation, and the like, may be used. In the oxidation good liquid-gas contact is desired but it is normally adequate to bubble finely-dispersed oxidant through the liquid obtained from the addition reaction. The oxidant normally is bubbled through for a sufficient time to convert the al—C$_2$H$_5$ bonds substantially completely to al—O—C$_2$H$_5$ bonds or to any selected degree of partial completion which is suitable for the particular situation. Since complete oxidation can be time consuming, frequently it is desired to convert only a portion of the al—$C_2H_5$ bonds into al—O—$C_2H_5$ bonds whereby improvement is realized by materially reducing the liberation of ethane upon hydrolysis although such liberation may not be eliminated entirely.

In the foregoing, the notation "al" is used to indicate one bond of the aluminum, there being three such al bonds per molecule of Al.

The following examples indicate preferred embodiments and aspects of the present invention.

EXAMPLE I

50 Millimols of sodium aluminum diethyl dihydride (26.5 wt. percent in toluene) and 50 millimols of ethyl acetate (20 mol percent in toluene) were reacted in the addition step of a typical reduction reaction. The sodium aluminum diethyl dihydride solution was placed in a 100 milliliter three-neck flask under nitrogen. The flask was in an ice bath and was equipped with a magnetic stirrer. The ethyl acetate was added to the flask dropwise over a period of about 5 minutes, the rate of addition being controlled to avoid exceeding 25° C within the flask. Following the ethyl acetate addition, the ice bath was removed and the flask heated to 50° C and maintained at that temperature for 1 hour to complete the addition reaction.

Following the addition, the flask and its contents were cooled to 25° C, and air was passed into the liquid contents of the flask at the rate of 0.3 liter per minute for 1 hour while maintaining a flask temperature of 25° C. A second oxidation step was then conducted using the same air rate but maintaining a temperature of 50° C for 1 hour. Following the oxidation, a wet test meter was connected to the flask to measure the volume of off-gas and a solution of 10 percent NaOH in water was added to the flask slowly until the evolution of gas stopped, indicating completion of the hydrolysis. The volume of gas liberated as measured by the wet test meter was 570 milliliters.

EXAMPLE II

In a comparative example, Example I was repeated using only one stage of oxidation of 1 hour at 25° C. On the subsequent hydrolysis, the gas liberated water was 1040 milliliters.

EXAMPLE III

In another comparative example, Example I was repeated without any oxidation between the addition and hydrolysis steps. In this instance the volume of gas liberated on hydrolysis was 1930 milliliters. From this set of comparative examples it is evident that the amount of ethane off-gas released on hydrolysis was substantially reduced when using the oxidation procedure as herein described.

I claim:

1. In a process for reducing a reducible compound by an addition reaction to $NaAlEt_2H_2$ followed by hydrolysis to remove the aluminum and recovering a reduced product, the improvement wherein the product from the addition reaction is subjected to oxidation with molecular oxygen prior to the hydrolysis whereby al—$C_2H_5$ bonds contained therein are converted to al—O—$C_2H_5$ bonds.

2. The process of claim 1 wherein the oxidation is at a temperature of from about −25° C to about 200° C.

3. The process of claim 1 wherein the oxidation is at a temperature of from 0° C to about 100° C.

4. The process of claim 1 wherein the oxidation is at a temperature of from about 25° C to about 50° C.

* * * * *